(12) United States Patent
Suzuki et al.

(10) Patent No.: US 8,603,821 B2
(45) Date of Patent: Dec. 10, 2013

(54) METHOD FOR PREPARING SERUM AND SERUM PREPARATION APPARATUS

(75) Inventors: Koji Suzuki, Hiroshima (JP); Seishin Tanaka, Hiroshima (JP); Satoshi Hirai, Hiroshima (JP); Mari Takabatake, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 695 days.

(21) Appl. No.: 12/529,664

(22) PCT Filed: Mar. 5, 2008

(86) PCT No.: PCT/JP2008/053972
§ 371 (c)(1), (2), (4) Date: Sep. 2, 2009

(87) PCT Pub. No.: WO2008/108412
PCT Pub. Date: Sep. 12, 2008

(65) Prior Publication Data
US 2010/0120150 A1 May 13, 2010

(30) Foreign Application Priority Data
Mar. 7, 2007 (JP) ................................. 2007-057071

(51) Int. Cl.
*C12N 5/00* (2006.01)
*A61K 35/14* (2006.01)

(52) U.S. Cl.
USPC ............................. 435/405; 435/408; 424/532

(58) Field of Classification Search
None
See application file for complete search history.

(56) References Cited

U.S. PATENT DOCUMENTS

| 5,100,564 | A | 3/1992 | Pall et al. |
| 5,527,472 | A | 6/1996 | Bellotti et al. |
| 6,214,338 | B1 | 4/2001 | Antanavich et al. |
| 7,678,780 | B2 * | 3/2010 | Mishra ........................... 514/120 |
| 2006/0039990 | A1 | 2/2006 | Barrueta et al. |
| 2006/0229547 | A1 | 10/2006 | Lynn et al. |
| 2006/0251622 | A1 * | 11/2006 | Suzuki et al. ................. 424/93.2 |
| 2009/0075355 | A1 * | 3/2009 | Suzuki et al. ................. 435/183 |

FOREIGN PATENT DOCUMENTS

| CN | 1110867 A | 10/1995 |
| EP | 1 625 861 A1 | 2/2006 |
| JP | H09509432 A | 9/1997 |
| JP | 2000-228 | 1/2000 |
| JP | 2003-55237 | 2/2003 |
| JP | 2004-89495 | 3/2004 |
| JP | 2006-014106 | 4/2006 |
| JP | 3788479 | 6/2006 |
| KR | 10-2006-0090453 A | 11/2006 |
| WO | WO-96/17871 | 6/1996 |
| WO | WO-2004/103439 | 12/2004 |
| WO | WO-2004/103440 | 12/2004 |
| WO | WO 2005/065242 A2 | 7/2005 |
| WO | WO 2005/105121 | * 11/2005 |
| WO | WO 2006/054448 | * 5/2006 |

OTHER PUBLICATIONS

McAlinden et al., "Comparison of Cancellous Bone-Derived Cell Proliferation in Autologous Human and Fetal Bovine Serum", Cell Transplantation 9 : 445-451 (2000).*
The Engineering ToolBox, "Sound Power, Intensity and Pressure", http://www.engineeringtoolbox.com/sound-power-intensity-pressure-d_57.html 1 page accessed Aug. 22, 2012.*
Lovette et al., "The Subcellular Distribution and Partial Characterization of Cholinesterase Activities of Canine Platelets", Biochimica et Biophysica Acta 428: 355-368 (1976).*
Notice of Reasons for Rejection issued to CN Application No. 200880006822.3, mailed Jul. 1,2011.
Notice of Reasons for Rejection issued to KR Application No. 10-2009-7020759, mailed Mar. 8, 2011.
N. Mizuno et al., "Human autologous serum obtained using a completely closed bag system as a substitute for foetal calf serum in human mesenchymal stem cell cultures", Cell Biology International, Academic Press, GB, vol. 30, No. 6, Jun. 1, 2006, pp. 521-524.
J. Ito et al., "Increased content of epidermal growth factor in platelet lysates in non-insulin-dependent diabetes mellitus", Life Sciences, Pergamon Press, Oxford, GB, vol. 53, No. 9, Jan. 1, 1993, pp. 717-724.
Hirai et al., "Review on concentration of cell growth factors in human serum prepared using a closed system human serum preparation device," Regenerative Medicine, Feb. 19, 2007, p. 306, p. 405, vol. 6.
European Office Action for European Application No. 08 721 392.2 dated Mar. 28, 2013.
Japanese Office Action for Japanese Application No. 2008-055554 with English translation dated Mar. 14, 2013.
Moritz M W et al., "Factors influencing shear-induced platelet alterations: platelet lysis is independent of platelet aggragation and release", Thrombosis Research, Tarrytown, NY, US, vol. 22, No. 4, May 15, 1981, p. 445-455.

* cited by examiner

*Primary Examiner* — Sandra Saucier
(74) *Attorney, Agent, or Firm* — Muncy, Geissler, Olds & Lowe, PLLC (57) ABSTRACT

A method for preparing serum and a serum preparation apparatus is provided that can give a large amount of serum with high culture efficiency regardless of freshness of blood used. In a method for preparing serum from blood containing at least platelets, a platelet processing step is provided in which platelet membrane in the blood is destroyed. After the platelet processing step, a deposition step for depositing thermolabile protein in blood and a removal step for removing the thermolabile protein, which has been deposited in the deposition step, are preferably provided.

2 Claims, 9 Drawing Sheets

METHOD FOR PREPARING SERUM AND SERUM PREPARATION APPARATUS

TECHNICAL FIELD

The present invention relates to a method for preparing serum from collected blood and a serum preparation apparatus.

BACKGROUND ART

Currently, in the field of regenerative medicine, studies in which stem cells collected from a subject are caused to proliferate or differentiate ex vivo, and are thereafter transplanted into a subject, thereby promoting regeneration of tissue of the subject, have been carried out.

In ex vivo cultural proliferation of stem cells, adding serum to the medium is known to improve culture efficiency.

As a method of preparing such serum, a method in which a blood collection tube is used that contains a blood coagulation accelerating solid, such as glass powder, is disclosed in Japanese Unexamined Patent Application Publication No. 2000-000228 (Patent Document 1). In addition, a method in which: platelets are activated by bringing collected blood into contact with a blood coagulation accelerating solid such as glass beads; cell growth factors are released; and then serum is separated, is disclosed in Japanese Patent No. 3788479 (Patent Document 2).

DISCLOSURE OF THE INVENTION

Problems to be Solved by the Invention

However, the method disclosed in Patent Document 1 aims at a blood test and therefore assumes preparation of serum from a low capacity blood collection tube. In a case of preparing serum according to the method disclosed in Patent Document 1, a preparation process must be repeatedly performed in order to obtain serum in an amount required for stem cell culture. Hence, the method is not suited for practical applications.

On the other hand, efficiency of cell culture depends on the amount of cell growth factors contained in serum. Even if a large amount of serum can be obtained at once, it is difficult to improve the culture efficiency if the amount of the cell growth factors is small. The cell growth factors are contained in platelets. The amount of the cell growth factors that are released therefrom depends on an activity state of the platelets, which depends on freshness thereof. In the method disclosed in Patent Document 2, since the platelets are spontaneously activated by bringing blood into contact with glass beads, if old blood is used, it is difficult to obtain the cell growth factors in an amount expected based on the amount of the platelets in blood and therefore a large amount of serum that can provide high culture efficiency cannot be obtained at once.

In addition, in the method disclosed in Patent Document 2, by bringing collected blood into contact with glass beads, platelets are activated and blood coagulation factors adhere to glass beads and are removed. In consequence, it is difficult to apply the method to anticoagulated blood such as donated blood, because, in such blood, blood coagulation factors cannot be removed by adhesion to glass beads.

The present invention is made in view of the aforementioned problems, and aims at providing a method for preparing serum and a serum preparation apparatus that can give a large amount of serum with high culture efficiency regardless of freshness of blood used.

Means for Solving the Problems

The present inventors have achieved the present invention based on the discovery that, even from old blood, it is possible to obtain cell growth factors in an amount expected based on the amount of platelets by destroying platelet membrane, in other words it is possible to obtain almost all cell growth factors contained in the platelets, and that, even anticoagulated blood can be used by performing a predetermined process thereon. More specifically, the present invention provides the following.

In a first aspect of the present invention, a method for preparing serum from blood containing at least platelets includes: a platelet processing step in which platelet membrane in the blood is destroyed.

According to a second aspect of the present invention, in the method for preparing serum as described in the first aspect, the platelet processing step is a step of performing on the blood at least one of: heat treatment; ultrasonic treatment; centrifugal treatment; compression and decompression treatment; and mixing and agitation treatment using glass beads.

According to a third aspect of the present invention, in the method for preparing serum as described in the first or the second aspect, anticoagulated blood is used as the blood.

According to a fourth aspect of the present invention, the method for preparing serum as described in any one of the first to the third aspects further includes a deposition step in which thermolabile protein in the blood, which is processed in the platelet processing step, is deposited.

According to a fifth aspect of the present invention, the method for preparing serum as described in the fourth aspect further includes a removal step in which the thermolabile protein, which is deposited in the deposition step, is removed.

In a sixth aspect of the present invention, serum is prepared according to the method for preparing serum as described in any one of the first to the fifth aspects.

In a seventh aspect of the present invention, a serum preparation apparatus for preparing serum from blood containing at least platelets includes: a blood reservoir portion that retains the blood; and a component storage portion that is connected with the blood reservoir portion aseptically and airtightly, and stores serum that is separated from blood retained in the blood reservoir portion.

According to an eighth aspect of the present invention, in the serum preparation apparatus as described in the seventh aspect, the blood reservoir portion includes: a whole blood reservoir portion that retains whole blood; and a plasma reservoir portion that is connected with the whole blood reservoir portion aseptically and airtightly, and retains plateletrich plasma that is separated from the whole blood retained in the whole blood reservoir portion.

According to a ninth aspect of the present invention, in the serum preparation apparatus as described in the seventh aspect, the blood reservoir portion is a plasma reservoir portion that retains platelet-rich plasma.

According to a tenth aspect of the present invention, in the serum preparation apparatus as described in any one of the seventh to the ninth aspects, the blood reservoir portion and the component storage portion are connected with each other by a connection portion that allows detachment and attachment thereof.

As used herein, the term "blood" indicates whole blood composed of hemocytes (erythrocytes and leucocytes) and plasma (serum) as a liquid component which include at least platelets, and a liquid containing at least one of these (for example, blood collected by apheresis), which include at least platelets.

Furthermore, the term "serum" used herein means: a pale yellow liquid obtained by allowing collected blood to stand, resulting in a reduction in fluidity, followed by separation from the red coagulated block (clot); or a pale yellow humoral component of blood, which is rich in cell growth factors.

In addition, the term "platelet-rich plasma" used herein indicates a humoral component of blood containing a greater concentration of platelets than normal whole blood.

Effects of the Invention

According to the present invention, a method for preparing serum and a serum preparation apparatus can be provided that can give a large amount of serum with high culture efficiency regardless of freshness of blood used.

In addition, according to the present invention, since serum can be prepared even from anticoagulated blood such as blood collected by apheresis, production of serum is possible without too much demand on a patient's body who has a difficulty in providing whole blood due to a condition thereof.

PREFERRED MODE FOR CARRYING OUT THE INVENTION

Embodiments of the present invention are explained hereinafter; however, the present invention is not limited thereto and can be modified and implemented within a scope of the aim thereof. It should be noted that, although description of similar parts is not repeated, it is not intended to limit the effect of the present invention.

First Embodiment

Method for Preparing Serum

The present invention is a method for preparing serum from blood containing at least platelets, including a platelet processing step in which platelet membrane in the blood is destroyed.

The amount of cell growth factors that platelets can release spontaneously depends on freshness of the platelets. Platelets in blood are composed of active, young platelets and less active, old platelets. The young platelets can spontaneously release more cell growth factors. Since the amount of old platelets increases over time after collecting blood, serum produced using old blood will be low in cell growth factors. However, in the invention according to the present embodiment, by providing a platelet processing step in which platelet membrane is destroyed, almost all cell growth factors expected based on the amount of platelets can be obtained regardless of freshness of blood (platelets) used. This can give serum with high culture efficiency.

As the platelet processing step, applying physical stress such as: heat treatment; ultrasonic treatment; centrifugal treatment; compression and decompression treatment; and the like can be exemplified. Among these, heat treatment and ultrasonic treatment that can efficiently destroy cell membranes are preferable. More specifically, a freezing and thawing method can be exemplified as the heat treatment.

The freezing and thawing method is a treatment in which a step of freezing and a step of thawing are each performed at least once. In the step of freezing, freezing temperature is in a range of $-196°$ C. to $-1°$ C., preferably in a range of $-80°$ C. to $-5°$ C. Frozen state holding time is, although dependent on content, preferably at least 1 second. On the other hand, in the step of thawing, thawing temperature is in a range of $0°$ C. to $56°$ C., preferably in a range of $4°$ C. to $37°$ C. Thawed state holding time is, although dependent on content, preferably at least 1 second.

In addition, the ultrasonic treatment is performed for 5 to 60 minutes, preferably 10 to 30 minutes, under a condition where ultrasound with respect to an object has sound pressure of at least 5 mV, which is measured by a sound pressure meter. In the present invention, the ultrasound is generated using a conventional ultrasonic generator.

In the centrifugal treatment, blood is contained in a container such as a blood bag, and the container is subjected to centrifugal separation under a condition of 10000 to 100000 G and 5 to 600 minutes. In a case where the centrifugal treatment is adopted as the platelet processing step, it is preferable to use platelet-rich plasma as blood.

In the compression and decompression treatment, a step of applying a relatively high pressure of 3 to 275 MPa to blood and then decompressing is performed at least once. This can efficiently destroy platelet membrane.

As a process of applying physical stress, mixing and agitation treatment can be exemplified in which glass beads are mixed into blood and the blood containing the glass beads is agitated by a centrifugal separator or the like.

The platelet processing steps are preferably performed directly on a container such as a blood bag containing collected blood. This can avoid contamination of collected or processed blood due to contact with open air. In addition, since transfer of blood into another container is not needed, the overall process can be simplified.

As used in the present embodiment, "blood" is not particularly limited as long as at least platelets are contained therein, and can be either whole blood or a blood component such as platelet-rich plasma. The blood can be several milliliters of blood collected by a collection tube for example; however, in a case of producing a large amount of serum at once, it is preferable to use hundreds of milliliters to thousands of milliliters of blood collected by a so-called blood bag.

Furthermore, the blood can be anticoagulated blood such as donated blood. As used herein, the term "anticoagulated" indicates that an anticoagulant such as CPD solution (Citrate-Phosphate-Dextrose solution), ACD-A solution (Acid-Citrate-Dextrose-A solution) is added to collected blood. The anticoagulant is preferably added in advance to a blood bag, which contains collected blood. The anticoagulant can be removed by neutralization, by adding calcium ions, which are derived from calcium chloride or the like, to blood processed in the platelet processing step.

In the present embodiment, since an anticoagulant is added to collected blood, a blood component to be obtained would contain thermolabile protein such as fibrinogen if the blood is used as is. If serum is kept in a state of containing thermolabile protein, fibrin is deposited and cell culturing will be difficult. Therefore, blood that is processed in the platelet processing step is preferably subjected to a deposition step in order to deposit the thermolabile protein, and then subjected to a removal step in order to remove the thermolabile protein.

Accordingly, even in a case where blood with an anticoagulant added thereto is used, the thermolabile protein can thus be removed without adding the abovementioned agent. As the thermolabile protein, fibrinogen and complement components can be exemplified.

For a similar reason to that explained with regard to the platelet processing step, the deposition step is also preferably performed directly on a container such as a blood bag, a collection tube or the like containing collected blood.

As the deposition step, a heating process can be exemplified. A heating condition depends on freshness and amount of blood that is used; however, in general, a heating temperature is preferably in a range of 45° C. to 65° C., more preferably in a range of 50° C. to 60° C., and most preferably in a range of 55° C. to 60° C. In addition, heating time is preferably in a range of 10 to 60 minutes, more preferably in a range of 20 to 50 minutes, and most preferably in a range of 30 to 40 minutes. Accordingly, the thermolabile protein can easily be deposited. In addition, since complement can be deactivated, there is no need to inactivate a prepared serum once again, thereby simplifying the step. For such a reason, the heating process can be performed under a similar condition to that of a so-called inactivation (at 56° C. for 30 minutes).

As the removal step, processes such as centrifugal separation, filtration and the like can be exemplified. Conditions for centrifugal separation may be defined according to the amount of prepared serum and type of the components to be separated; however, they may be defined to be, for example, 4400 g×6 minutes, at 22° C. Filtration is preferably performed using, for example, a filter having a pore diameter of 200 μm.

Second Embodiment

The present embodiment is different from the first embodiment in that serum is prepared without adding an anticoagulant.

In the present embodiment, blood that is processed in the platelet processing step is in a hemolytic state in which cell membranes, not only of platelets but also of erythrocyte and leucocyte, are destroyed. Consequently, in order to remove hemoglobin in erythrocyte and DNA and RNA in leucocyte, a process for removing component derived from erythrocyte and leucocyte is provided between the platelet processing step and the deposition step. More specifically, removal is performed using an absorption column, a filter or the like. It should be noted that an absorption column is preferably used for removing hemoglobin, and a filter is preferably used for removing DNA and RNA.

Third Embodiment

Serum Preparation Apparatus

Next, a serum preparation apparatus that prepares the abovementioned serum according to the present invention is described.

The serum preparation apparatus according to the present invention is a serum preparation apparatus for preparing serum from blood containing at least platelets, including: a blood reservoir portion that retains the blood; and a component storage portion that is connected with the blood reservoir portion aseptically and airtightly, and stores serum that is separated from blood retained in the blood reservoir portion. A serum preparation apparatus according to the present embodiment is described in detail hereinafter.

Figure 1:
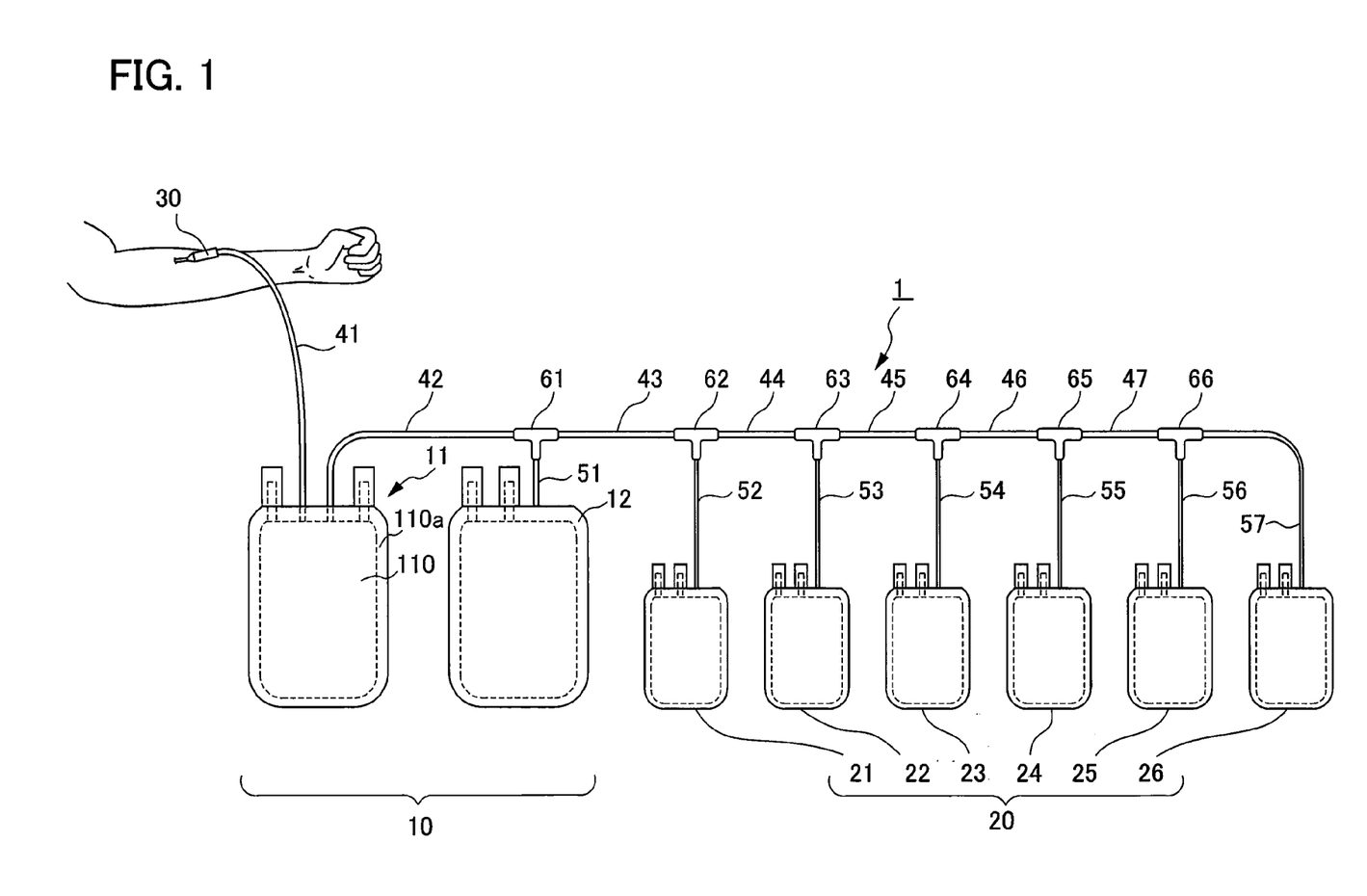
FIG. 1 is a view illustrating a serum preparation apparatus according to a third embodiment of the present invention.

FIG. 1 is a view illustrating a serum preparation apparatus 1 according to the present embodiment. The serum preparation apparatus 1 comprises a blood reservoir portion 10, and a component storage portion 20 as main elements. The blood reservoir portion 10 is composed of a whole blood reservoir portion 11 that retains whole blood of a subject and a plasma reservoir portion that retains platelet-rich plasma separated from the whole blood. Among these, the whole blood reservoir portion 11 is constituted of a main body portion 110 formed with two sheets of a flexible resin material, for example, soft polyvinylchloride, fused to each other at an external marginal portion 110a to give a bag shape. As the whole blood reservoir portion 11, the plasma reservoir portion 12 is also made of soft polyvinylchloride. It should be noted that the whole blood reservoir portion 11 can be a so-called blood bag filled with an anticoagulant or a transfer bag. Inside of the blood reservoir portion 10 is sterilized in advance. In the blood reservoir portion 10 used in the present embodiment, an anticoagulant is added thereto in advance.

The component storage portion 20 is composed of six bag bodies 21 to 26; each of which is made of soft polyvinylchloride as the whole blood reservoir portion 11. As with the blood reservoir portion 10, these are similarly sterilized in advance.

As shown in FIG. 1, at the upper edge end of the main body portion 110 of the whole blood reservoir portion 11, two tubes 41 and 42 are connected in an air-tight manner to the connection ports thereof. The tube 41 among them serves as an introducing path for introducing the blood, and accordingly, a needle for collecting blood 30 or a junction, which can be connected to a needle for collecting blood, is connected at the other end thereof. The other tube 42 is connected to each of the bags 21 to 26 via tubes 43 to 47 and 51 to 57, and branches 61 to 66. These serve as transferring paths for transferring blood. These tubes 41 to 47 and 51 to 57 are constituted from a resin material having flexibility, for example, soft polyvinylchloride. In this configuration, the bags 21 to 26 and each of the tubes 51 to 57 of the component storage portion 20 are also connected in an air-tight manner.

The whole blood reservoir portion 11 and the plasma reservoir portion 12, and the plasma reservoir portion 12 and the bag bodies 21 to 26, are connected with each other via the tubes 42 to 47 and 51 to 57, in a state where inner space thereof is isolated from external environment, in other words in an airtight manner. In addition, the tubes 42 to 47 and 51 to 57, and the branches 61 to 66 are also connected in a state where a region thereinside, through which blood components pass, is isolated from outer environment. As a method for connecting thereof, solvent adhesion, thermal welding, ultrasonic welding and the like can be exemplified.

Although not shown in FIG. 1, the serum preparation apparatus 1 according to the first embodiment of the present invention is configured so that a flow path can be switched by clamping an appropriate part of the tubes 42 to 47, and 51 to 57, when blood and serum that is extracted is transferred.

Serum Preparation Process

The serum preparation process using the serum preparation apparatus 1 having the aforementioned configuration is explained hereinafter with reference to FIGS. 1 to 3. Reference numerals referred herein are of FIG. 1, unless otherwise stated.

Figure 2:
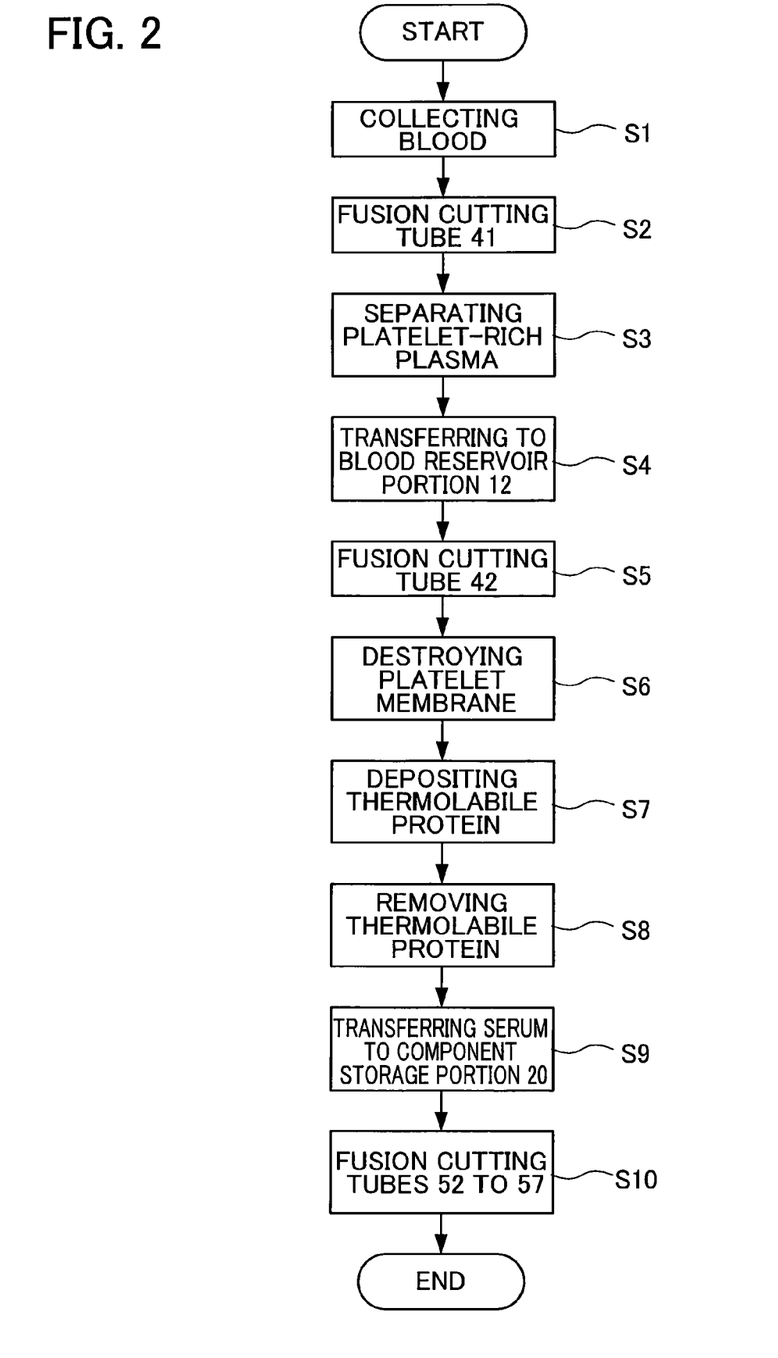
FIG. 2 is a view illustrating steps from collection of blood to storage of serum, using the serum preparation apparatus according to the third embodiment of the present invention.

As shown in FIG. 2, the blood separation process using the aforementioned serum preparation apparatus 1 includes ten steps (S1 to S10) as generally classified.

First, in the first step of the process, a blood collection needle 30 is inserted into a subject (patient), and blood is collected. In this step, the blood collected from the blood collection needle 30 is stored in the whole blood reservoir portion 11, which is positioned on a lower side, via the tube 41 (hereinafter referred to as a retention step S1). Here, a breakable partition wall (not shown) is provided in the tube 42, in the vicinity of a boundary with the whole blood reservoir portion 11, so that blood retained in the whole blood reservoir portion 11 does not flow into the plasma reservoir portion 12. Alternatively, the tube 42 has a clamp or the like closing a path on the whole blood reservoir portion 11 side. The retention step S1 is terminated after the required amount has been collected, taking into account the patient's physical condition and the like upon collecting the blood. As used herein, the required amount is approximately 200 to 600 ml when the physical constitution and physical condition of the patient are problem free.

It should be noted that a blood collection apparatus, which is widely used for blood donation, can also be used for collecting blood.

Next, the blood collection needle 30 is removed from the subject, and then a part of the tube 41 connecting the blood collection needle 30 with the whole blood reservoir portion 11 is cut and fused, sealing its cut edge at the same time (hereinafter referred to as a first fusion cutting step S2). It should be noted that a fusion cutting apparatus (a so-called sealer) can be used for fusion cutting of the tube 41.

Subsequently, plasma (hereinafter in the present embodiment, platelet-rich plasma) is separated from the whole blood in the whole blood reservoir portion 11 (hereinafter referred to as a first separation step S3). As a method for separation, centrifugal separation, filtration, a combination thereof, and the like can be exemplified. In the present embodiment, centrifugal separation is performed. Conditions for centrifugal separation may be defined according to the amount of retained blood and type of the components to be separated; however, they may be defined to be, for example, 1100 (G)×6 (min.), at 24° C. It should be noted that, in case of centrifugal separation, the serum preparation apparatus 1 is preferably folded and set to a centrifugal separator.

Thereafter, the platelet-rich plasma that is separated is transferred to the plasma reservoir portion 12 (hereinafter referred to as a first transfer step S4). The present step is described with reference to FIG. 3.

Figure 3:
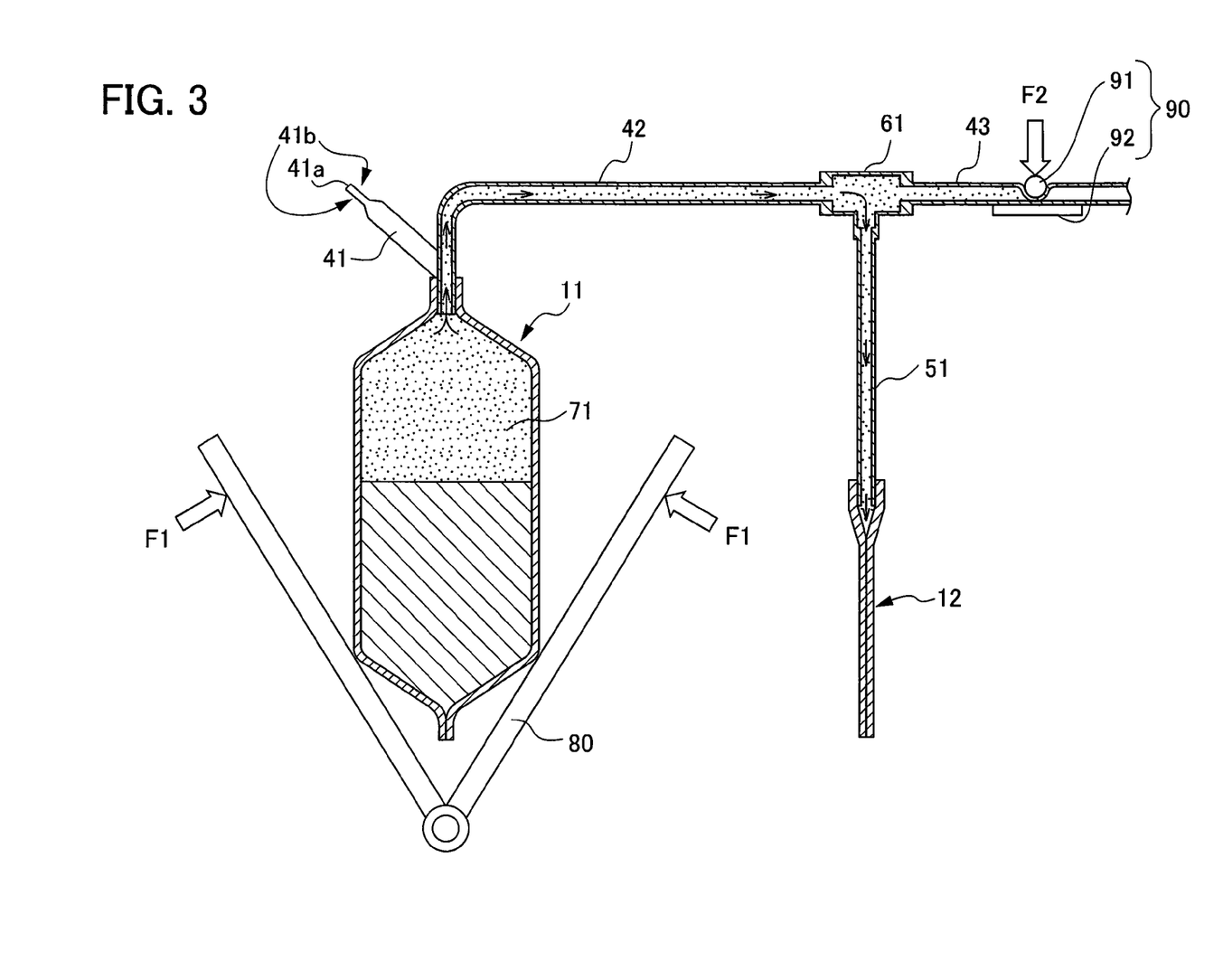
FIG. 3 is a cross-sectional view illustrating a method for transferring platelet-rich plasma 71, which is prepared in a whole blood reservoir portion 11 of the serum preparation apparatus according to the third embodiment of the present invention, to a plasma reservoir portion 12.

As shown in FIG. 3, when the platelet-rich plasma 71 that is separated is to be transferred to the plasma reservoir portion 12, the whole blood reservoir portion 11 is compressed (F1) by a compressor 80 disposed outside the whole blood reservoir portion 11, while the path of the tube 43 is closed by using a clamp 90. As described above, after the retention step S1, the tube 41 that is connected to the whole blood reservoir portion 11 in an air-tight manner has a mid-flow 41a being cut and fused, and a cut edge and a vicinity thereof 41b being sealed at the same time.

By thus being compressed (F1), a part of the platelet-rich plasma 71, which is a supernatant extracted by separation, is transferred to the plasma reservoir portion 12 through the tube 42, the branch 61, and the tube 51.

It should be noted that the path of the tube 43 is closed by pinching the flexible tube 43 between a disk 91 and a base 92 of the clamp 90.

Blood components such as erythrocyte remaining in the whole blood reservoir portion 11 after the transfer of the platelet-rich plasma 71 can be diluted with saline or the like and returned to a donor's body. Alternatively, the remaining blood component, to which an erythrocyte preservative solution is added, can be stored for a predetermined period of time and returned to a donor's body, for example in a case of cell transplantation.

Referring to FIG. 2 again, after the plasma reservoir portion 12 is filled with the platelet-rich plasma 71, the tube 42 is fusion-cut and sealed (hereinafter referred to as a second fusion cutting step S5). The fusion cutting process and the sealing process are performed as in the first fusion cutting step S2.

Thereafter, platelet membrane in the platelet-rich plasma, which has been transferred to the plasma reservoir portion 12, is physically destroyed (hereinafter referred to as a platelet processing step S6). As the platelet processing step S6, heat treatment, ultrasonic treatment, centrifugal treatment, compression and decompression treatment, and mixing and agitation treatment using glass beads can be exemplified. In the present embodiment, the platelets are processed by a freezing and thawing method as the heat treatment. In the freezing and thawing method, a step is repeated three times in which the whole serum preparation apparatus 1 is frozen at −80° C. for 60 minutes and then heated up to 37° C. and held for 20 minutes.

In the platelet processing step S6, platelet membrane is destroyed and cell growth factors in the platelets are released. Accordingly, almost all cell growth factors included in the platelets can be obtained regardless of freshness of platelets or blood.

Next, thermolabile protein in the blood, which is processed in the platelet processing step S6, is deposited (hereinafter referred to as a deposition step S7). A deposition process is performed by heating the plasma reservoir portion 12, which is processed in the platelet processing step S6. In the present embodiment, a heating process is performed at 56° C. for 30 minutes. In the deposition step S7, not only the thermolabile protein but also complement can be inactivated. By inactivating complement, an influence on a cultured cell can be alleviated.

It should be noted that, in the heating process in the deposition step S7, the whole serum preparation apparatus 1 can be heated.

Subsequently, the thermolabile protein, which is deposited in the deposition step S7, is removed (hereinafter referred to as a removal step S8). As a method for removal, filtration, centrifugal separation, a combination thereof, and the like can be exemplified. In the present embodiment, centrifugal separation is performed at 4400 (G) for six minutes. In centrifugal separation, the whole serum preparation apparatus 1 is preferably included in a centrifugal separator. In a case where filtration is performed, by embedding a filter in a part of a tube 43 in FIG. 1, the thermolabile protein that is deposited can be removed during a second transfer step (described later).

Thereafter, the serum separated in the removal step S8 is transferred to the bags 21 to 26 of the component storage portion 20 (the second transfer step S9). A method of transfer is preferably pushing out the prepared serum by applying pressure on the outside of the plasma reservoir portion 12, as in the first transfer step S4. The serum can be stored in each of the bags 21 to 26. It should be noted that, in a case where the prepared serum is small in amount, number of bags to be used among the bags 21 to 26 can be adjusted by clamping or the like any of the tubes 44 to 47.

After transferring the serum to the component storage portion 20, the tubes 52 to 57 are fusion-cut and sealed (hereinafter referred to as a third fusion cutting step S10). The fusion cutting process and the sealing process are performed as in the first fusion cutting step S2.

According to the present embodiment, serum can be produced aseptically from the collected blood, without exposing open air. Accordingly, since a series of procedures from blood collection to serum preparation can be performed without exposing open air, a risk of microbial contamination can be reduced.

In the present embodiment, the freezing and thawing method is exemplified as the heat treatment in the platelet processing step S6. However, the heat treatment in the present invention is not limited to the freezing and thawing method. For example, a heating process, performed as the heat treatment, can also achieve the effect of the present invention. The heating process in the platelet processing step S6 is performed, for example, by heating the whole serum preparation apparatus 1 at 56° C. for 60 minutes. This can destroy platelet membrane and provide cell growth factors from the platelets. Alternatively, by performing a heating process at 56° C. for 60 minutes in the platelet processing step S6, procedures of the deposition step S7 can be performed at the same time. This can shorten a series of procedures in the serum preparation step.

It should be noted that the serum preparation apparatus according to the present invention can be used for blood of mammals such as rodents, domestic animals, primates and the like, and thus can be used as a blood component separation apparatus for nonhuman animal.

Fourth Embodiment

Figure 4:
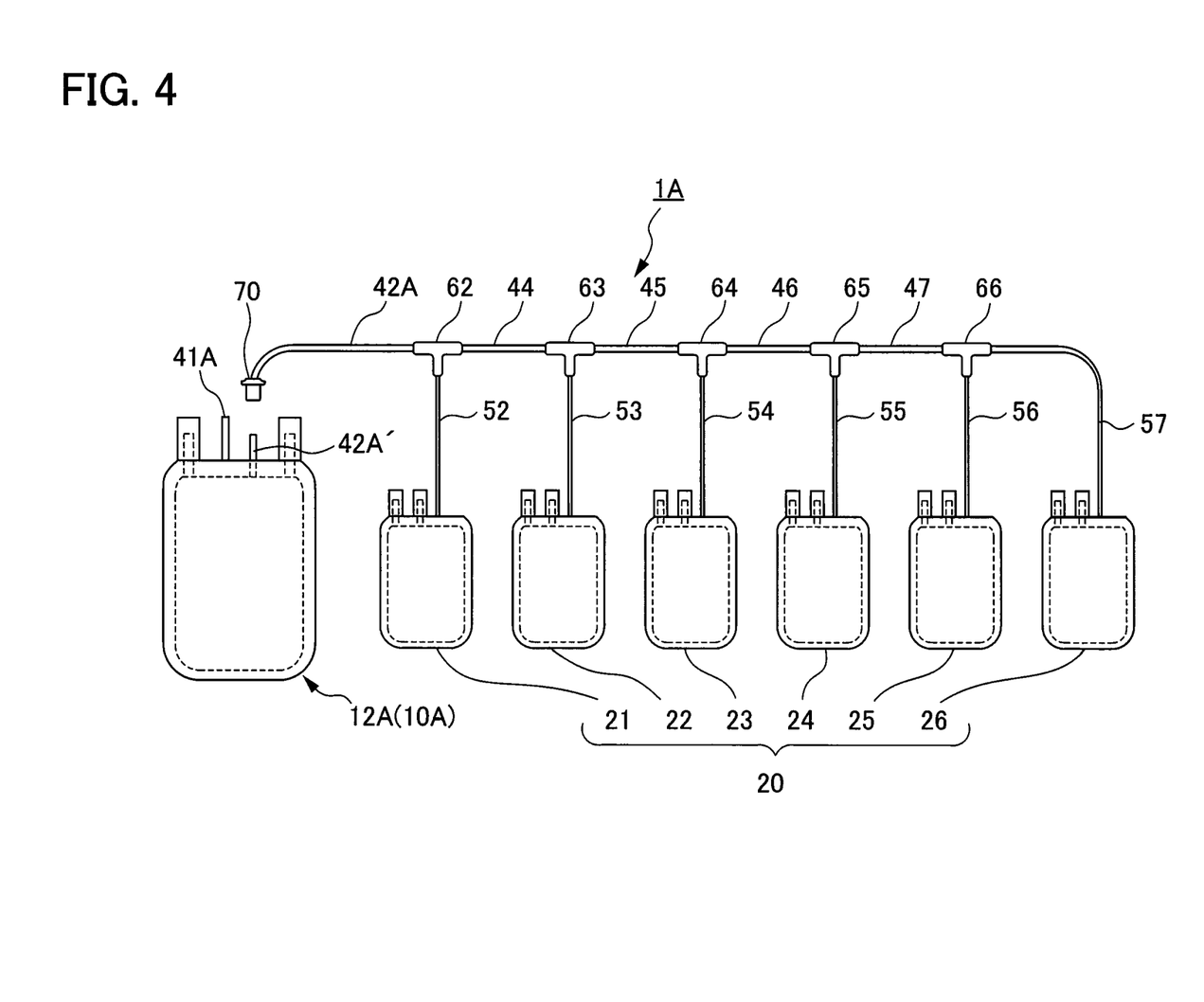
FIG. 4 is a view illustrating a state where the plasma reservoir portion is detached in a serum preparation apparatus according to a fourth embodiment of the present invention.
Figure 5:
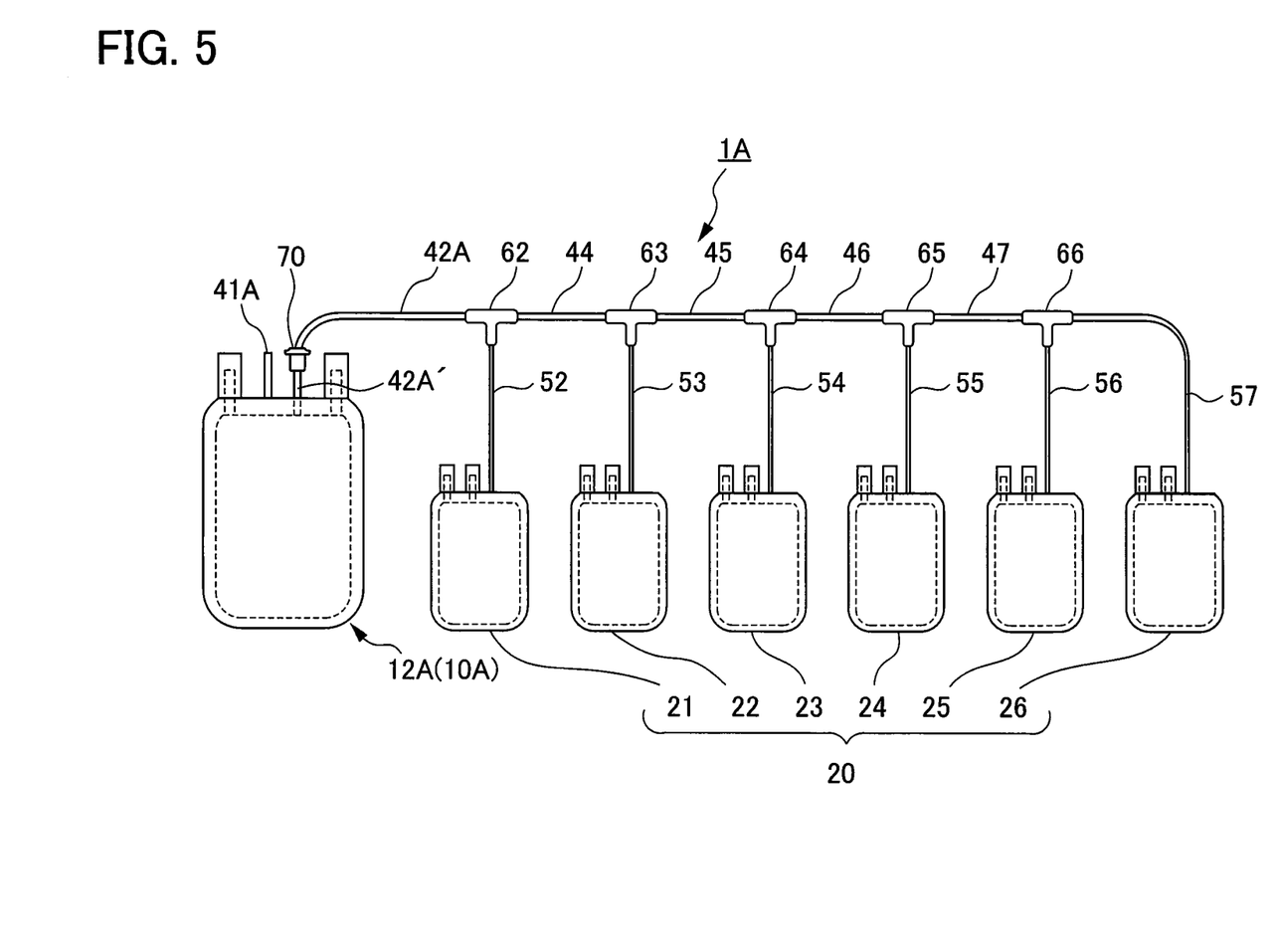
FIG. 5 is a view illustrating a state where the plasma reservoir portion is attached in the serum preparation apparatus according to the fourth embodiment of the present invention.

FIGS. 4 and 5 are views illustrating a serum preparation apparatus 1A according to the fourth embodiment of the present invention. The present embodiment is different from the third embodiment in that a blood reservoir portion 10A is composed of a single bag, not of a whole blood reservoir portion and a plasma reservoir portion, in other words the blood reservoir portion 10A is composed only of a plasma reservoir portion 12A that retains platelet-rich plasma. In FIG. 4, in the plasma reservoir portion 12A, for example, platelet-rich plasma collected by apheresis donation is retained. In this case, a tube 42A is not connected in advance with the platelet reservoir portion 12A. Before use, the tube 42A is inserted into a connection portion 70 so as to connect with a tube 42A' on a side to the plasma reservoir portion 12A. It should be noted that a tube 41A, which is used for collecting blood, is preferably fusion-cut in advance. As the connection portion 70, for example, a configuration provided with an air-tight coinjection port that has a function of opening and closing a slit-shaped opening of a valving element along with insertion and removal of an insertion member (see Japanese Patent No. 3389983) can be exemplified.

Figure 6:
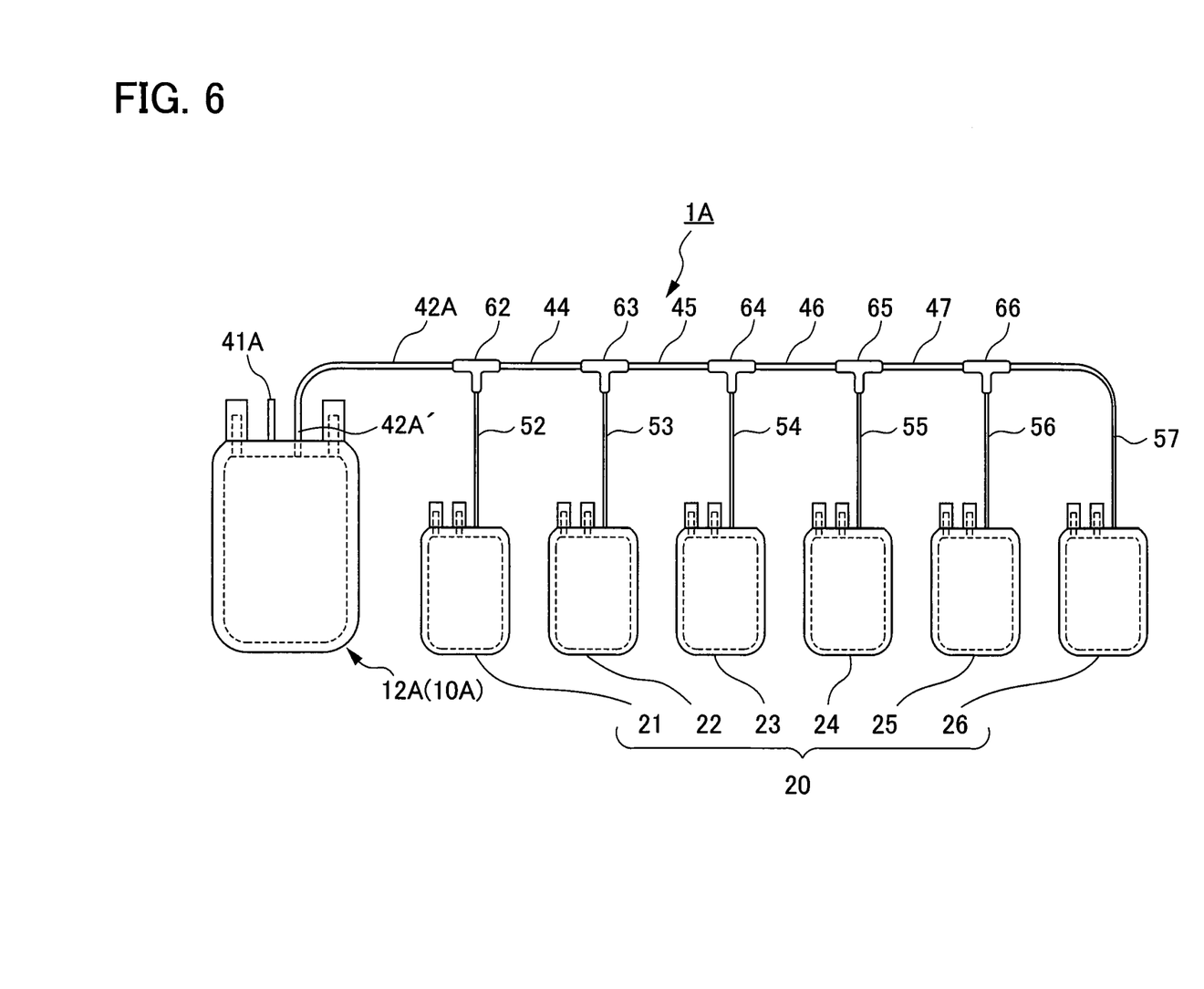
FIG. 6 is a view illustrating a modification of the serum preparation apparatus according to the fourth embodiment of the present invention.

It should be noted that, in the present embodiment, the plasma reservoir portion 12A and the tube 42A can be configured to be connected with each other integrally in advance without the connection portion 70, as shown in FIG. 6.

In such a configuration, blood collected outside such as donated blood can be used. In addition, since blood collected by apheresis can be used, serum can be easily prepared from blood of a patient who has a difficulty in providing whole blood due to a condition thereof. Other configurations in the present embodiment are similar to that of the serum preparation apparatus according to the third embodiment, and therefore description thereof is omitted.

Fifth Embodiment

Figure 7:
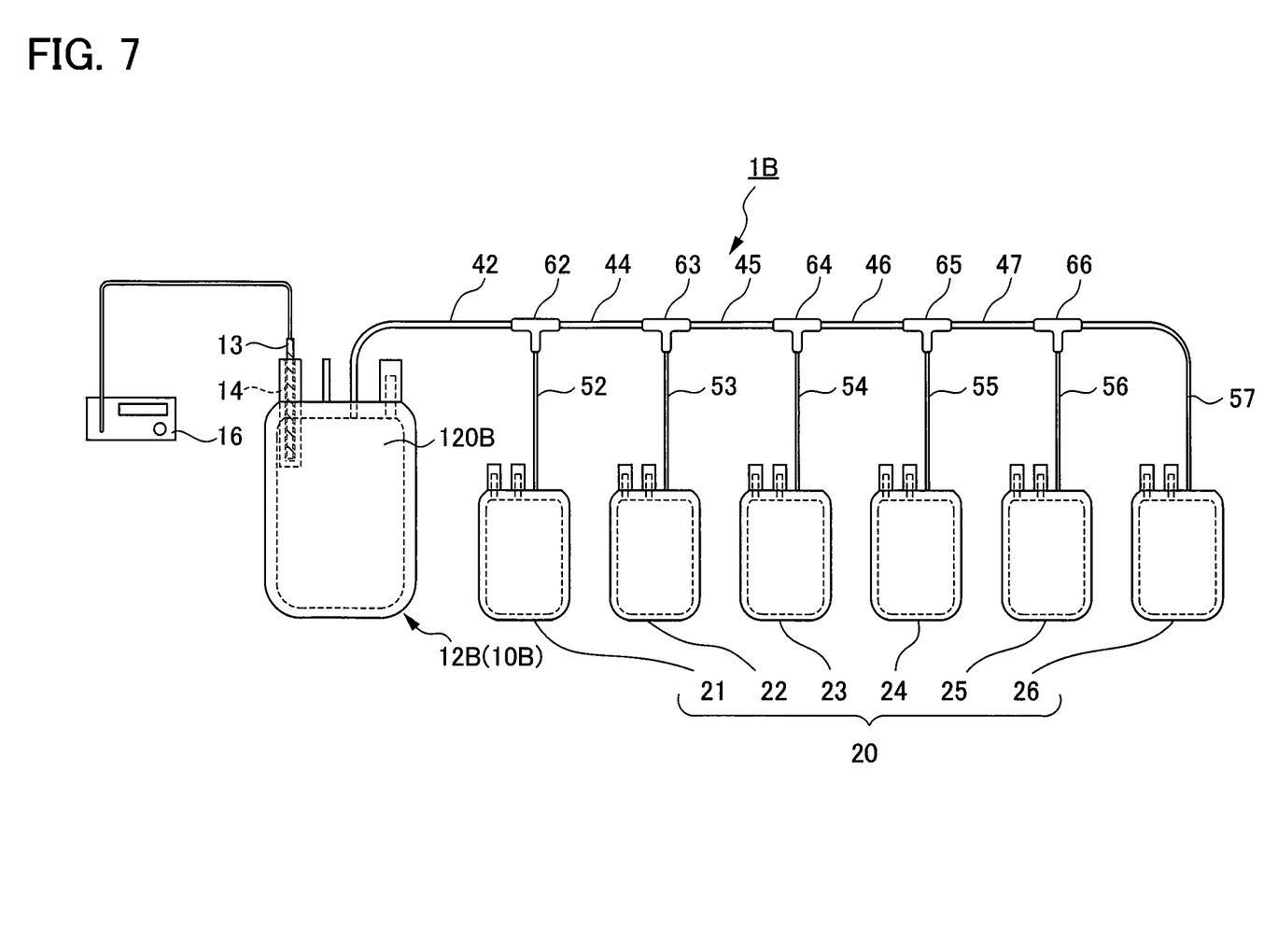
FIG. 7 is a view illustrating a serum preparation apparatus according to a fifth embodiment of the present invention.
Figure 8:
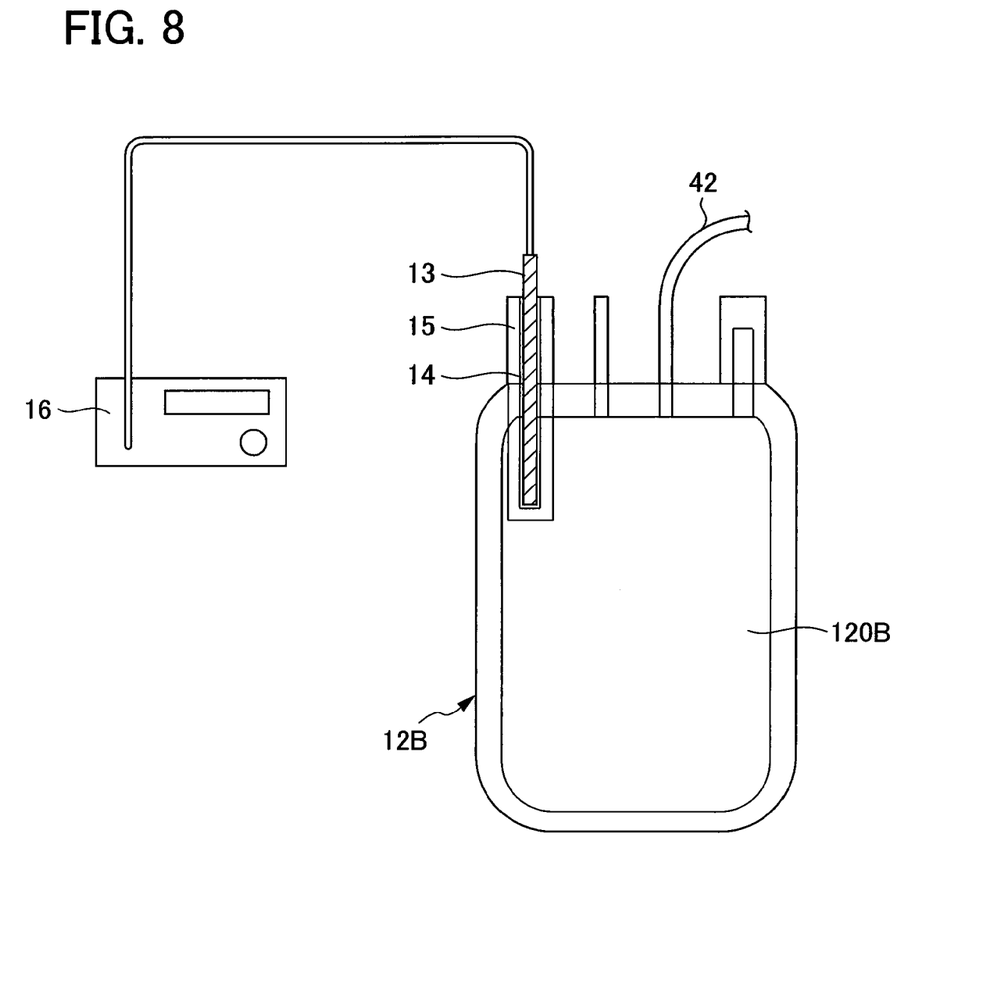
FIG. 8 is a partial enlarged view of FIG. 7.

FIGS. 7 and 8 are views illustrating a serum preparation apparatus 1B according to a fifth embodiment of the present invention.

The present embodiment is different from the first embodiment in that a blood reservoir portion 10B is composed only of a plasma reservoir portion 12B, and that an ultrasonic radiator storage portion 14 that can store an ultrasonic transducer 13, which generates ultrasound, is provided in the plasma reservoir portion 12B.

The ultrasonic radiator storage portion 14 is formed such that a cylindrical member 15, with a closed end and an open end, is disposed from an upper edge portion 12B of the plasma reservoir portion so as to project toward the inside of a main body portion 120B, which is formed in a bag shape. The cylindrical member 15 is disposed so that a side to the closed end projects toward the inside of the main body portion 120B.

The ultrasonic radiator 13 is rod-shaped and inserted from the open end into a hollow portion of the cylindrical member 15. In other words, in the present embodiment, the hollow portion of the cylindrical member 15 constitutes the ultrasonic radiator storage portion 14.

A shape of the hollow portion of the cylindrical member 15 is substantially identical to an outer shape of the ultrasonic radiator 13. Accordingly, in a case where the ultrasonic radiator 13 is stored in the ultrasonic radiator storage portion 14, the ultrasonic radiator 13 closely contacts the cylindrical member 15.

The ultrasonic radiator 13 is connected with an ultrasonic generator main body 16 via a connecting wire and generates ultrasound in response to an operation on a switch provided on the ultrasonic generator main body 16.

In the abovementioned configuration, ultrasound generated by the ultrasonic radiator 13 can be directly applied to whole blood retained inside the main body portion 120B. This allows an efficient serum preparation process. As a result, energy resource required for the serum preparation process and time for serum preparation can be reduced.

In addition, the ultrasonic radiator storage portion 14 can be connected in a state where an inner space of the plasma reservoir portion 12B is isolated from an outer space thereof. In such a configuration, a platelet processing step can be performed while maintaining sterility of the inner space of the plasma reservoir portion 12B.

Furthermore, by disposing the ultrasonic radiator storage portion 14 in the plasma reservoir portion 12B, which is the blood reservoir portion 10B of the serum preparation apparatus 1B, the ultrasonic radiator 13 used for ultrasonic treatment in the plasma processing step can be easily attached to and removed from the serum preparation apparatus 1B, thus facilitating the serum preparation process. Moreover, a compact ultrasonic generator can be used for size reduction of the serum preparation apparatus 1B.

EXAMPLES

Examples 1 to 4, Comparative Example 1, Reference Examples 1 and 2

Methods for destroying platelet membrane in a platelet processing step were examined.

To begin with, platelet-rich plasma was separated from whole blood. First, 1.4 ml of CPD solution was added to 10 ml of human blood and the mixture was centrifuged at 20° C. and 3500 rpm, for 8 minutes (with a centrifugal separator manufactured by Kubota Corporation). Next, a plasma layer and a buffy coat layer were separated and centrifuged at 20° C. and 800 rpm, for 8 minutes. A supernatant was separated as platelet-rich plasma. A test sample was thus obtained.

1 ml of the abovementioned platelet-rich plasma was dispensed in each container and subjected to the following processes. It should be noted that a processing method adopted in Comparative Example 1 is a method disclosed in Patent Document 2 (Japanese Patent No. 3788479).

(Example 1) a process of freezing at −80° C. for 10 minutes and then thawing at 37° C. was performed 3 times (Example 2) ultrasonic treatment was performed for 15 minutes (Example 3) ultrasonic treatment was performed for 30 minutes (Example 4) a process of violently agitating in a container containing a large number of glass beads of 1 mm in diameter was performed (Comparative Example 1) five glass beads of 4 mm in diameter and 10 µl of Calcium Chloride of 27.8 w/v % was added thereto and heated at 37° C. for 30 minutes (Reference Example 1) centrifugal separation at 14000 G, for 10 minutes was performed once (Reference Example 2) centrifugal separation at 14000 G, for 10 minutes was performed three times After performing the abovementioned processing, centrifugal separation at 3500 rpm for 10 minutes was performed and quantity of cell growth factors in a supernatant (serum) was determined. The results are shown in Table 1.

TABLE 1

| Quantity of Cell Growth Factors | Example 1 | Example 2 | Example 3 | Example 4 | Comparative Example 1 | Reference Example 1 | Reference Example 2 |
|---|---|---|---|---|---|---|---|
| TGF-β1 (pg/ml) | 37900 | 62193.3 | 62066.7 | 44173.3 | 44915.6 | 193.3 | 4966.7 |
| PDGF-BB (pg/ml) | 3792.9 | 5652.1 | 5672.1 | 1637.9 | 3325 | 0 | 0 |

The sample processed by the freezing and thawing method (Example 1) and the sample processed by adding the glass beads and agitating (Example 4) could give substantially same quantity of cell growth factors as in the conventional method (Comparative Example 1). On the other hand, the sample processed by the ultrasonic treatment in Examples 2 and 3 could give cell growth factors in an amount that is almost equal to an upper limit of cell growth factors contained in human serum.

Figure 9:
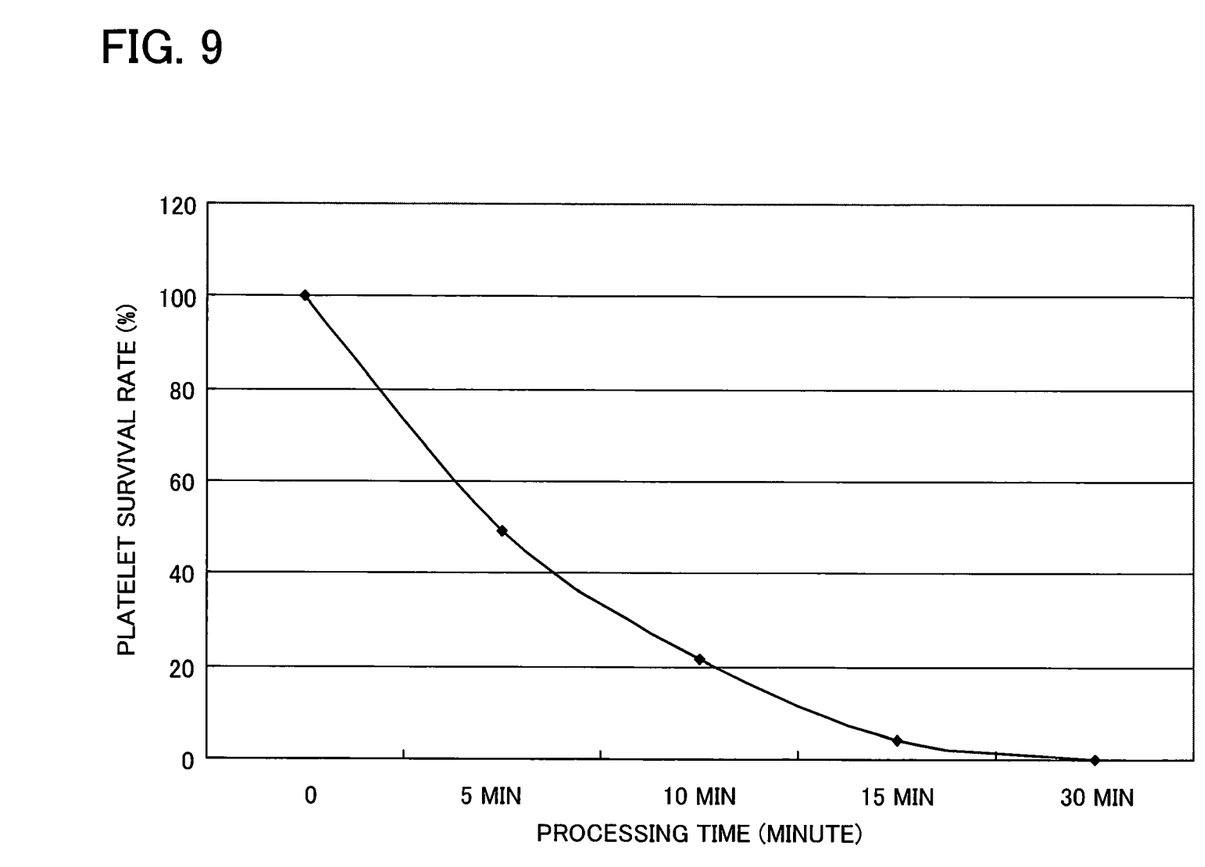
FIG. 9 is a view illustrating a relationship between elapsed time of ultrasonic treatment and platelet survival rate (%) in Examples 2 and 3.

Subsequently, regarding Examples 2 and 3, a relationship between elapsed time of ultrasonic treatment and platelet survival rate (%) was examined. FIG. 9 is a view illustrating a relationship between elapsed time of ultrasonic treatment and platelet survival rate (%) (n=5). This shows that almost all platelet membrane was destroyed by 15 minutes of ultrasonic treatment.

The invention claimed is:

1. A method for preparing serum from blood or a blood component containing platelets to which an anticoagulant has been added, comprising:
    a platelet destroying step in which platelet membranes in the blood or blood component are destroyed;
    a deposition step in which fibrin in the blood or blood component is deposited by heating blood or blood component processed in the platelet destroying step at 45° C. to 65° C.; and
    a removing step in which the fibrin, which is deposited in the deposition step, is removed,
    wherein the platelet destroying step is a step of performing on the blood or the blood component ultrasonic treatment or compression and decompression treatment.

2. The method for preparing serum as described in claim 1, wherein the compression and decompression treatment comprises applying a pressure of 3 to 275 MPa to the blood or blood component and then decompressing the blood or blood component, this process being performed at least once.

* * * * *